United States Patent [19]
Kurtze et al.
[11] Patent Number: 4,858,597
[45] Date of Patent: Aug. 22, 1989

[54] PIEZOELECTRIC TRANSDUCER FOR THE DESTRUCTION OF CONCRETIONS WITHIN AN ANIMAL BODY

[75] Inventors: Günther Kurtze, Winheim; Rainer Riedlinger, Karlsruhe, both of Fed. Rep. of Germany

[73] Assignee: Richard Wolf GmbH, Knittlingen, Fed. Rep. of Germany

[21] Appl. No.: 253,884

[22] Filed: Oct. 5, 1988

Related U.S. Application Data

[63] Continuation of Ser. No. 614,145, May 25, 1984, abandoned.

[30] Foreign Application Priority Data

Jun. 1, 1983 [DE] Fed. Rep. of Germany ....... 3319871

[51] Int. Cl.[4] ........ A61B 17/22
[52] U.S. Cl. ........ 128/24 A; 128/328
[58] Field of Search ........ 128/6, 24 A, 328, 660

[56] References Cited

U.S. PATENT DOCUMENTS

| | | | |
|---|---|---|---|
| 2,792,829 | 5/1957 | Calosi | 128/24 A |
| 3,237,623 | 3/1966 | Gordon | 128/24 A |
| 3,735,755 | 5/1983 | Eggleton . | |
| 3,942,531 | 3/1976 | Hoff et al. . | |
| 4,094,306 | 6/1978 | Kossoff | 128/24 A |
| 4,205,686 | 6/1980 | Harris et al. | 128/660 |
| 4,281,550 | 8/1981 | Erikson | 128/660 |
| 4,311,147 | 1/1982 | Hausler | 128/328 |
| 4,315,514 | 2/1982 | Drewes et al. | 128/24 A |
| 4,340,944 | 7/1982 | Dory | 367/96 |
| 4,375,818 | 3/1983 | Suwaki et al. | 128/660 |
| 4,385,255 | 5/1983 | Yamaguchi et al. | 128/660 |
| 4,417,582 | 11/1983 | Trimmer et al. | 128/660 |
| 4,440,025 | 4/1984 | Hayakawa et al. | 128/660 |
| 4,462,092 | 7/1984 | Kawabuchi . | |
| 4,474,180 | 10/1984 | Angulo | 128/328 |
| 4,484,569 | 11/1984 | Driller et al. . | |
| 4,526,168 | 7/1985 | Hassler et al. | 128/303 R |
| 4,617,931 | 10/1986 | Dory | 128/328 |

FOREIGN PATENT DOCUMENTS

| | | | |
|---|---|---|---|
| 654673 | 12/1937 | Fed. Rep. of Germany | 128/24 A |
| 2351247 | 8/1976 | Fed. Rep. of Germany . | |
| 2921444 | 11/1980 | Fed. Rep. of Germany . | |

OTHER PUBLICATIONS

"Attempted Disintegration of Calculi by Ultrasonic Vibrations", Mulvaney, J. of Urology, Nov. 1953, pp. 704–707.
"The Application of Ultrasonic Energy to Urinary and Biliary Calculi", Coats, J. of Urology, May 1956, pp. 865–874.
"Current Status of Mechanical Lithotripsy", Howards et al., Transactions of the Amer. Assoc. of G.-Ur. Surgeons, 1973, pp. 123–125.
"Ultrasound Transducers for Pulse-Echo Medical Imaging", Hunt et al, IEEE, 1983, pp. 425–429.
"Use of Focused Ultrasound to Accelerate the Metering of a Cataract", Gavribu et al., Sov. Phys. Acoust., vol. 20, No. 3, 1974.
"High Speed pulse Technology", Früngel, vol. 1, 1965.

(List continued on next page.)

*Primary Examiner*—Max Hindenburg
*Attorney, Agent, or Firm*—Willian Brinks Olds Hofer Gilson & Lione

[57] ABSTRACT

A piezoelectric transducer in the form of a spheroidal cap comprises a mosaic of individual piezoceramic elements having a height of 3 to 10 mms and a lateral extension that does not substantially exceed the height there being gaps between the piezoceramic elements which are filled with an electrically insulating material having a modulus of elasticity which is smaller by at least one order of magnitude than that of the ceramic material, with the rise of the spheroidal cap amounting to at least 5 cms and the apex angle of the corresponding spherical sector amounting to at least 60°.

21 Claims, 2 Drawing Sheets

OTHER PUBLICATIONS

Therapeutic Ultrasound in the Production of Ocular Lesions, Lizzi et al., American Journal of Ophthamology, 86:185-192 (1978).

Applications of Therapeutic Ultrasound in Opthamology, Lizzi et al., Progress in Medical Ultrasound, vol. 2 (1981).

Ultrasound: Its Applications in Medicine and Biology, edited by Francis J. Fry, Elsevier Scientific Publishing Company (1978), vol. 3, pp. 689–707.

Therapeutic Ultrasound in the Production of Ocular Lesions, Lizzi et al., American Journal of Ophthamology, 86:185–192 (1978).

"Applications of Therapeutic Ultrasound in Ophthalmology": by Dr. Jackson Coleman et al. in Progress in Medical Ultrasound, vol. 2, 1981, pp. 263–270.

Precision High Intensity Focusing Ultrasonic Machines for Surgery, Frank J. Fry, American Journal of Physical Medicine, vol. 37, No. 3 (Jun. 1978).

Sources of High Intensity Ultrasound, edited by L. D. Rozenberg, vol. 1, Plenum Press, N.Y., N.Y. (1969).

Generating High-Energy Ultrasound Pulses with Focusing Piezo Transducers (including publication in original German, and translation), paper by R. Reidlinger et al., Third congress of the Federation of Acoustical Societies of Europe, Gottingen (1982).

Production of Deep Focal Lesions by Focused Ultrasound–Current Status by P. P. Lele, Ultrasonics (Apr. 1967), pp. 105–112.

PIEZOELECTRIC TRANSDUCER FOR THE DESTRUCTION OF CONCRETIONS WITHIN AN ANIMAL BODY

This is a continuation of Ser. No. 614,145, filed May 25, 1984, now abandoned.

BACKGROUND OF THE INVENTION

1. Field of the Invention

The invention relates to a piezoelectric transducer in the form of a spheroidal cap, for the location and destruction of hard concretions within an animal body, more particularly the human body. Thus, it should be understood that the term "animal" is used generically herein to embrace humans and what are commonly referred to as animals.

2. Description of the Prior Art

With comminutions of brittle solids formed within the body, e.g. such as kidney, bladder or gall stones, it is impossible without having an internal operation to destroy the same except by means of focussed ultrasonic oscillation. However, the application of focussed ultrasonic waves to the body should be undertaken with care to ensure that injurious energy densities fall directly on the object which is to be destroyed and do not harm or destroy normal healthy tissues. To achieve this object, it is known to use for example spark gaps under water as sound sources, and to concentrate the ultrasonic emission on the locus of the concretion by means by an elliptically shaped reflector. This method has the disadvantage that the shock waves generated by spark gaps are reproducible only with difficulty and, consequently, may be metered also with difficulty, and that concentration on targets of minimum size is impossible in view of the size of the bubble formed during spark discharge. Furthermore, the bubbles produced have to be eliminated between two consecutive shock waves, and the spark gaps utilised have a very short service life only (e.g. 100 discharges).

A second known possibility consists in making use of ultrasonic transducers as sound sources, which either have the form of spheroidal caps or are focussed by application of lens systems. However, the greatest difficulty during application of ultrasonic transmitters consists in securing the high energy densities required. According to experience, pressure amplitudes of the order of magnitude of 2000 bar are needed for destruction of concretions. Lens systems are hardly applicable for this reason, because reflection and absorption in the lens material cause excessive losses. Ultrasonic transducers in the form of spheroidal caps are satisfactorily appropriate for the continuous emission of ultrasonic oscillation, but the application of continuous ultrasonic oscillation to a concretion formed within the body is impossible because burning of normal healthy body tissue in the vicinity of the concretion would be unavoidable at the high energy density required. In principle, shock waves may also be generated with ultrasonic transducers in the form of spheroidal caps, but this presupposes an extremely high load-bearing capacity of the transducer elements because the resonance increase of the oscillation amplitude occurring during continual energisation cannot be exploited whilst doing so. Ultrasonic transducers in the form of spheroidal caps are commonly produced as piezoceramic appliances, e.g. based on barium titanate, by being pressed into shape, sintered and then polarised radially. Since the variation in the thickness of the material caused by the action of the electrical charge applied is always combined with a transverse contraction at the same time, such spheroidal ceramic caps are destroyed very rapidly during pulse excitation at high voltages. Special measures are needed for this reason, to secure the high load-bearing capacity required.

On the other hand, piezoelectric transducers have the advantage that the pulses which they generate may be reproduced and metered perfectly and that their service life, subject to appropriate construction, is considerably greater than that of spark gaps. Another advantage of piezoelectric transmitters is that it is possible to utilise one and the same transmitter to generate the shock waves as well as to locate the concretion. Since different tissue structures have to be transirradiated between the surface of the body and the concretion, there is always the risk that the focus may be displaced by sound refraction, so that perfect alignment on the locus of the concretion, e.g. determined by X-rays, is possible. However, adjustment defects of this kind cannot arise, if ultrasonic pulses radiated at low power by the shock wave transducer itself are utilised for location.

Experience shows that it is inappropriate to expose the whole concretion which is to be destroyed to the shock wave at the same time, and that it is more advantageous to concentrate the power successively in chronological sequence on separate sections of the concretion. As a matter of fact, comparatively large fragments are formed in the first case, whereof the removal by natural means is frequently still impossible, whereas, in the second case, the concretion disintegrates into minute and almost dust-like fragments which may be removable by natural means. Accordingly, the main object of the invention consists in concentrating the sonic energy emitted by a piezoelectric transducer on a minimum cross-section and in limiting the required total output.

SUMMARY OF THE INVENTION

To this end, the present invention consists in a piezoelectric transducer for the destruction of hard concretions formed within an animal body, and being in the form of a spheroidal cap, characterized in that it comprises a mosaic of individual piezoceramic elements, each having a height of about 3 to about 10 mm and a lateral extension which does not substantially exceed the height, in that the piezoceramic elements have gaps therebetween which are filled with an elastic insulating material having a modulus of elasticity which is smaller by at least one order of magnitude than that of the ceramic material, and in that the rise (h) of the spheroidal cap is at least 5 cm and the apex angle ($\alpha$) of the corresponding spherical sector is at least 60°.

Preferably, the individual piezoelectric elements are of cylindrical form.

A piezoelectric transducer constructed in accordance with the intervention can be applied in such a manner that after an echo pulse location of the concretion in the body which is to be performed by means of the transducer, a first shock wave treatment lasting a few seconds is performed on an areal section of the concretion by supplying the transmitter with high-voltage pulses, after which one or more other areal sections of the concretion are treated with shock waves after a locating operation repeated in each case.

BRIEF DESCRIPTION OF THE DRAWINGS

In order that the invention may be more readily understood, reference will now be made, by way of example, to the accompanying drawings, wherein.

DESCRIPTION OF THE PREFERRED EMBODIMENT

Figure 1:
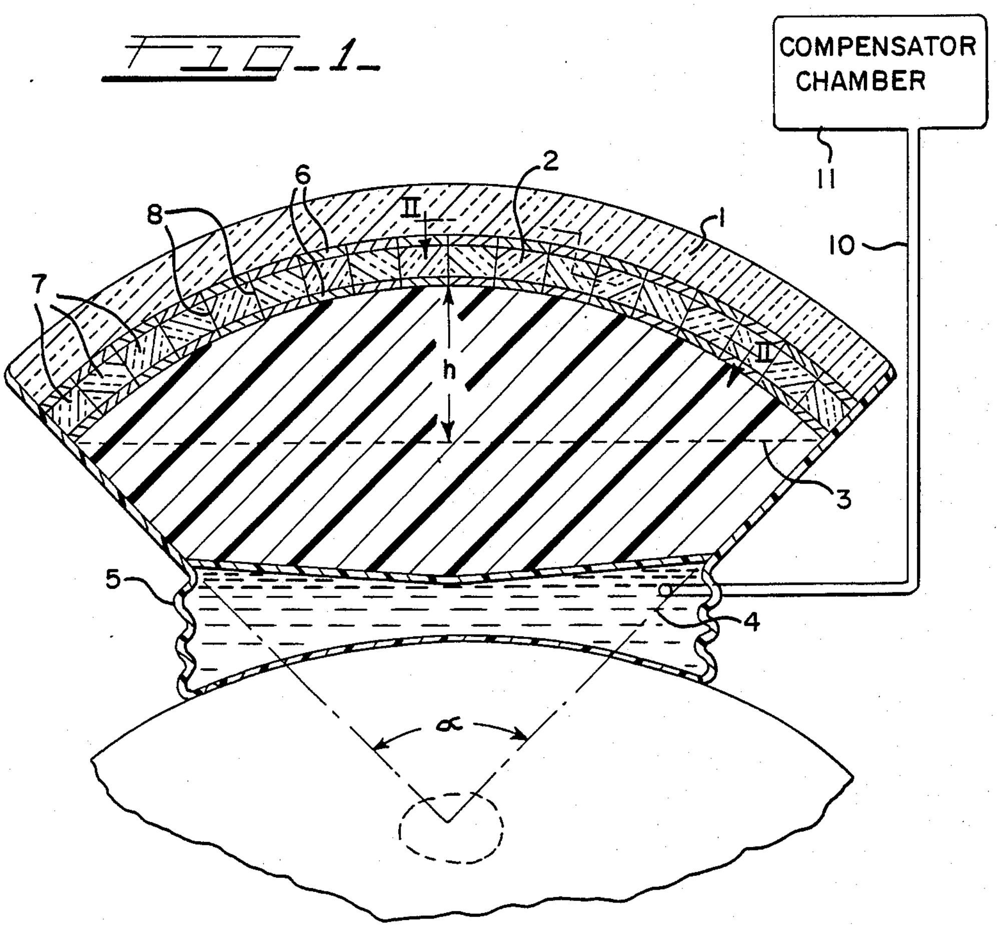
FIG. 1 is a cross-sectional view with portions in elevation for purposes of illustration of an apparatus according to the present invention.
Figure 2:
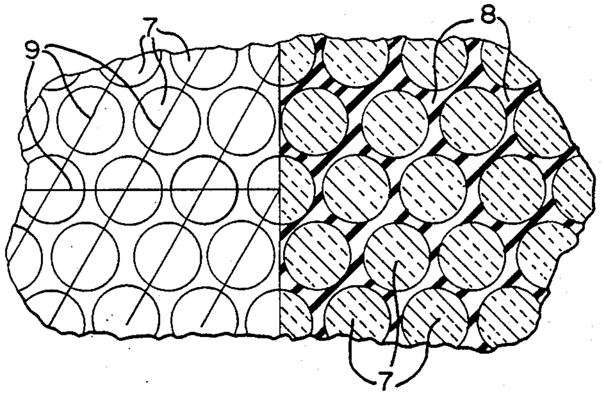
FIG. 2 is an enlarged partial view taken along lines II—II of FIG. 1 with the spacing between piezoceramic elements being exaggerated for purposes of illustration.

Referring to FIG. 1, a piezoelectrically acting layer 2 is situated on a supporting rear wall 1 produced as a spheroidal cap from robust electrically insulating material (e.g. GFK). The layer 2 comprises an arcuate mosaic of preferably cylindrical elements 7 (best illustrated in FIG. 2) of piezoceramic material having a height of say 3 to 10 mm. The transverse dimensions of the piezoceramic elements 7 should be no greater than their height, to minimise the shearing strains acting to destroy the transducer, which are engendered by resonance oscillations in peripheral direction. For the same reason, the gaps or spaces between the transducer elements 7 should be filled with an elastic material 8, e.g. silicone rubber, having a high electrical insulating capacity, and a modulus of elasticity which is smaller by at least one order of magnitude than that of the ceramic material. The two end faces 6 of the piezoceramic elements 7 are metallised to generate the energising electrical field strength, the inner electrode being intended to be at earth potential or ground. The cylindrical piezoelectric transducer elements 7 are connected to a source of electrical voltage, for example via a network of connecting wires 9.

The inside or recess 3 (FIG. 1) of the spheroidal cap 1 is filled with a liquid or a soft plastics material (e.g. a casting resin). The acoustic impedance of the filling should be matched as closely as possible to the resistance of the body tissue which is to be transirradiated. The surface of the plastics material layer should be shaped convexly so that air bubbles formed in a liquid layer 4 serving as a connection to the body may veer off sideways even under irradiation in the vertical direction so as not to obstruct the irradiation. The liquid layer 4 itself, may be of water, for example, and is enclosed between two diaphragms and a bellows-like rubber sleeve 5. The acoustic impedance of the liquid layer 4 should, again, be matched to that of the body tissue. To secure reliable connection to the surface of the body, it will commonly be necessary to connect the liquid-filled cavity between the plastics material layer and the rubber sleeve with a tube 10 extending to a compensator vessel 11, through which bubbles formed may also escape.

The size of the focal area obtainable depends on the depth or the rise h of the spheroidal cap, at a given pulse length. It has been shown by calculation that the size of the focal area amounts to say 5 $mm^2$ with a rise of 10 cm. For the reasons stated above, a rise of say 10 cm should consequently be aimed at.

Another dimension of importance for the configuration of the spheroidal cap is the apex angle $\alpha$ of the spherical sector between the cap and the focal point. This angle determines the degree of reduction of the sonic intensity with increasing distance from the focal point and is thus essential regarding the degree of risk to the surrounding tissues. Since it is unavoidable that a positive pressure surge is always followed by a negative pressure surge which for its part may generate cavitation and thereby may injure the tissue, it is necessary to undertake an evaluation at this juncture. As the frequency increases, the cavitation threshold rises very steeply above 100 kHz. It amounts to 10 bar at 100 kHz, 30 bar at 200 kHz, 200 bar at 500 kHz. At a height of 5 mms of the ceramic elements 7, the fundamental frequency of the transmitter is approximately 500 kHz. The oscillator is consequently intended for a pulse length of one microsecond. Assuming that the shock wave peak pressure amounts to 1000 bar in the focal plane in the negative pressure stage, and assuming an apex angle of 60°, it will still amount to approximately 200 bar at a distance from the focal plane of 10 mm in axial direction, but only 40 bar at a distance of 50 mm. Tissue damage caused by cavitation should thus no longer be expected even at a distance of 10 mm from the focal point.

For this reason, the apex angle of the spherical sector should amount to at least 60°.

Electrical excitation

Figure 3:
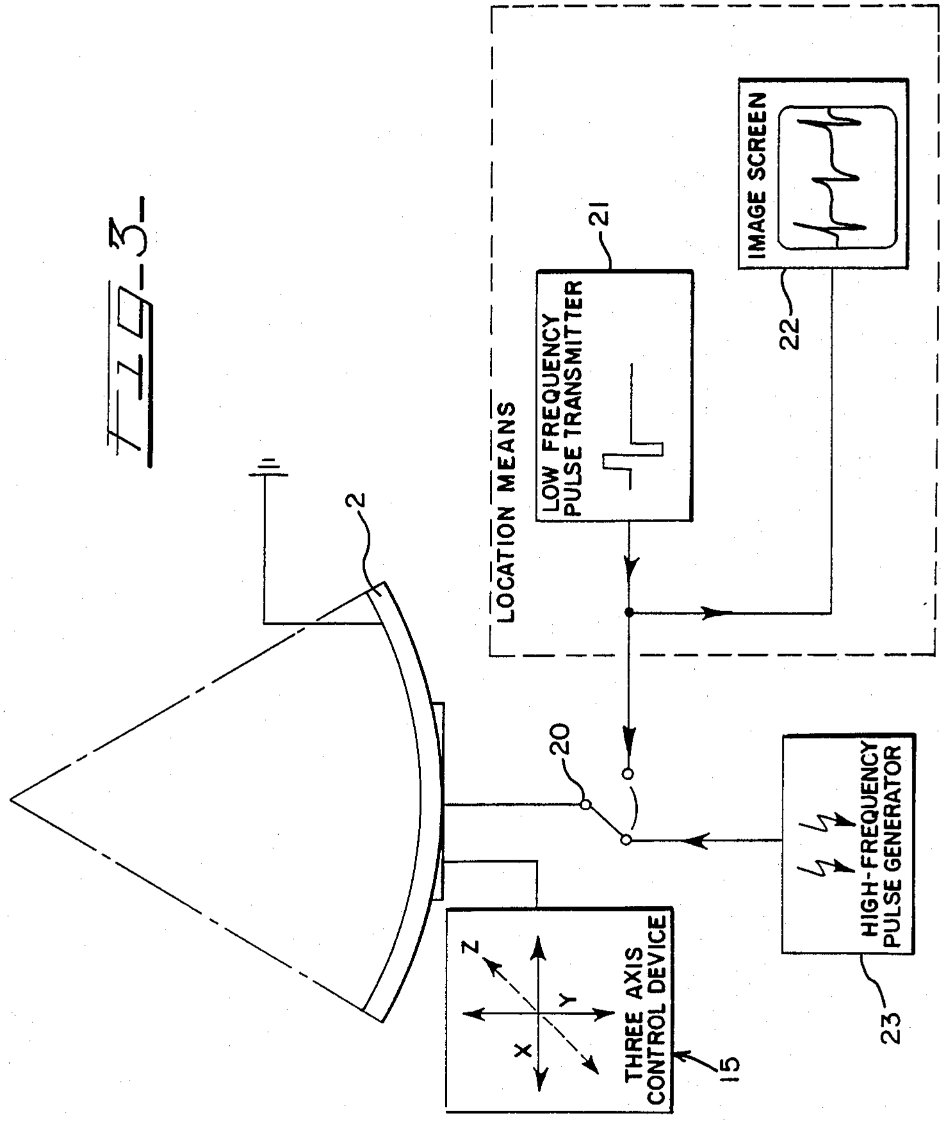
FIG. 3 is a schematic circuit diagram of the electrical system for operating the apparatus of FIG. 1.

The location of the concretion in the body is performed by feeding the transducer with oscillatory pulses from a pulse transmitter 21 of a location means (FIG. 3) through a switch 20, that is to say simply by setting the transmitter for a maximum value of the reflected pulse in all three coordinate directions under the approximate knowledge of the position of the concretion, e.g determined by X-ray photographs. The transducer 2 is moved in those three coordinate directions with a conventional three axis control device 15, shown schematically in FIG. 3, until these maximum values are achieved. The concretion then must mandatorily lie at the focal point. To this end, the oscillator is supplied with oscillatory pulses of low voltage at say 10 cycles of oscillation, e.g. of the frequency of the lowest natural transverse vibrations of the transmitter elements (500 kHz). This is followed by electronic switching to reception and indication of the reflected pulse on an image screen 22 of the location means. This location method may be improved, by automating the resetting of the transmitter to a maximum echo amplitude in each case.

The transmitter is supplied with high-frequency pulses from a high frequency pulse generator 23 to generate the shock waves. Since the pulse length is predetermined by the sonic travel period within the ceramic material, a high-voltage pulse having a rise time barely shorter than a microsecond and a decay time greater than a microsecond is adequate as an electrical supply. In the case of ceramic transducers of a thickness of 5 mm, a voltage of 6 to 10 kV is required.

A pulse of 2000 bar and a duration of one microsecond over a cross-section of 10 $mm^2$ corresponds to work of no more than approximately 0.3 watts-seconds.

A pulse sequence of say 10 pulses/seconds may consequently be emitted without worrying, since this would yield a constant rating of 3 watts at the focal point, consequently without any injurious localised heating.

Since, according to experience, approximately 1000 pulses are needed for destruction of a kidney stone, this means an actual treatment period of less than two minutes.

Method of Treatment

The apparatus suspended from a stand in such manner as to be movable in all three directions has its rubber diaphragm placed on the skin of the patient and coupled to the same via a film of liquid between the skin and diaphragm. No air bubbles may be included between the diaphragm and skin whilst doing so. It is assured that the diaphragm is in contact with the skin, throughout the area of the radiation cross-section, by means for obtaining appropriate liquid pressure (height adjustment of the compensator vessel 1). The apparatus is adjusted by means of the echo pulse location method in such a manner that the concretion lies at the focal point. The first shock wave treatment may thereupon be begun. Another locating action should occur after a treatment of a few seconds, a result possibly already secured being detectable whilst doing so, from the change in shape and amplitude of the reflected signal. Treatment is continued after renewed adjustment, and so on.

In the case of large concretions, sonic action should not be continued until complete destruction of the concretion has been obtained, since the risk arises that excessive quantities of dust or granulate could clog the natural outlets. A repetition of the treatment at adequate intervals of time is indicated in such cases.

It should be appreciated that modifications and variations may be made to the embodiment herein described without departing from the scope of the invention.

We claim:

1. A piezoelectric transducer for the destruction of hard concretions within an animal body, said piezoelectric transducer being in the form of a spheroidal cap with a rise and comprising a mosaic of separate piezoceramic elements each having a height of about 3 to about 10 mm and a lateral extension which does not substantially exceed the height, said piezoceramic elements having gaps therebetween, said gaps being filled with an electrically insulating elastic material having a modulus of elasticity which is smaller by at least one order of magnitude than that of the piezoceramic material, and the rise of the spheroidal cap being at least 5 cms and the apex angle of the corresponding spherical sector of the cap being at least 60°.

2. A piezoelectric transducer as claimed in claim 1, wherein the piezoceramic elements are of cylindrical form.

3. A piezoelectric transducer as claimed in claim 1, wherein the cap has a recess being filled with a soft plastics material to form a member having an acoustic impedance which is approximately equal to that of the body tissue and said member having a surface which is outwardly lightly domed convexly.

4. A piezoelectric transducer as claimed in claim 1, which includes a fluid-filled pad being provided for coupling to the body, said pad having an external elastomeric diaphragm, said fluid having an acoustic impedance which is approximately equal to that of the body tissue.

5. A piezoelectric transducer according to claim 1 wherein the cap has a recess filled with a soft plastic material having an acoustic impedance which is approximately equal to that of the body tissue to form a member having a surface which is outwardly, slightly domed convexly, and said transducer includes a fluid-filled pad adjacent to said surface to permit coupling to the body, said pad having an external elastomeric diaphragm, said fluid having an acoustic impedance which is approximately equal to that of the body issue.

6. An apparatus according to claim 8 wherein the cap has a recess being filled with a soft plastic material to form a member having an acoustic impedance which is approximately equal to that of the body tissue and said member having a surface which is outwardly slightly domed convexly.

7. An apparatus according to claim 6 which includes a fluid-filled pad adjacent the surface of the member to permit coupling to the body, said pad having an external elastomeric diaphragm, said fluid having an acoustic impedance which is approximately equal to that of the body tissue.

8. An apparatus for destroying hard concretions within an animal body, said apparatus including a piezoelectric transducer having a form of a spheroidal cap with a rise, said transducer comprising a mosaic of separate piezoceramic elements each having a height of a range of 3 to 10 mm and a lateral extension which does not substantially exceed the height, said piezoceramic elements having gaps therebetween, said gaps being filled with an electrically insulating elastic material having a modulus of elasticity which is smaller by at least one order of magnitude than that of the material of the elements, and the rise of the spheroidal cap being at least 5 cm and the apex angle of the corresponding spherical sector of the cap being at least 60°.

9. An apparatus according to claim 8 which includes means for adjusting the transducer for the generation of echo pulses for locating a concretion within a body cavity, and means for setting the transducer to generate shock waves for a few seconds following an echo pulse location.

10. An apparatus according to claim 9 wherein the means for adjusting and the means for setting are alternately activated repeatedly so that a location is determined and shock waves are generated and then a new location is determined and treated.

11. An apparatus according to claim 8 which includes means for transmitting oscillatory pulses of a duration of approximately 10 cycles and at least at the fundamental frequency and a multiple of the fundamental frequency of the transducer for the purpose of location, and for adjusting the transducer to maximum reflection.

12. An apparatus according to claim 8 wherein said transducer includes a pad for coupling to the body, said pad having elastomeric diaphragms forming a chamber containing a fluid having an acoustic impedance which is approximately equal to that of the body tissue, and means for obtaining the appropriate fluid pressure in the chamber including a compensator vessel being connected by a tube to the chamber so that changing the height of the vessel relative to the chamber varies the fluid pressure in the chamber.

13. A method of using an apparatus having a piezoelectric transducer for the destruction of hard concretions within an animal body, said transducer having a form of spheroidal cap with a rise and comprising a mosaic of separate piezoceramic elements each having a height of a range of 3 10 mm and a lateral extension which does not substantially exceed the height, the piezoceramic elements having gaps therebetween which are filled with an electrically insulating elastic material having a modulus of elasticity which is smaller by at least one order of magnitude than that of the ceramic material of the elements and the rise of the spheroidal cap being at least 5 cm and the apex angle of the corresponding spherical sector being at least 60°, said method comprising creating individual pressure pulses of a duration of 1 μs in the transducer to destroy the concretions by charging the transducer with a rise time $<<1$ μs and a voltage of a range of 5–15 kV and then discharging the transducer with a decay period of $>1$ μs.

14. A method according to claim 13 in which the steps of charging and then discharging are repeated cyclically at 1 to 20 times/second.

15. A method of destroying calculi from outside of a patient's body, comprising the steps of:

(a) fixing a plurality of individual piezoelectric elements, each having an inner end face, in a mosaic pattern on a support member, isolated from each other, so that each inner end face is substantially facing a common focal point over an included angle of at least sixty degrees and the inner end faces collectively define a generally spherical transmissive surface having a rise of at least five centimeters;

(b) determining the position of a calculus inside the patient's body by directing low power ultrasonic pulse waves into the body and viewing an image derived therefrom on an image screen;

(c) positioning said support member and transmissive surface outside the patient's body so that the focal point coincides with the determined position of said calculus inside the patient's body;

(d) exciting each of said elements with at least one high power electrical signal so that at least one discrete pulse is generated from said transmissive surface and focused at said focal point and no greater than about ten pulses per second are generated;

(e) transmitting said pulse through liquid interposed between said elements and the patients body to said focal point;

(f) redetermining the position of said calculus by directing low power ultrasonic waves into the body and viewing an image derived therefrom on said image screen;

(g) repositioning said arrangement if the position of the calculus has moved so that the focal point continues to coincide with the calculus;

(h) repeating steps (d) through (g) above until clinically beneficial calculus destruction has been achieved; and (i) at all times maintaining the pulse rate over time and the pulse power per pulse at levels which, in total, destroy the calculus without clinically significant injury to tissue.

16. A lithotrite for contact-free, pulsed wave disintegration of calculi without producing clinically significant injury to tissue without an animal body, comprising;

(a) a high power, ultrasonic pulse generator;

(b) a piezoelectric transducer formed by a mosaic of piezoelectric elements separated from each other by gaps and mounted on a rear member so as to form a spherical transmissive surface portion adapted to focus the disintegrating waves at a focal spot spaced from the transmissive surface portion; and (c) means substantially enclosing said spherical transmissive surface portion and said gaps;

(d) said enclosing means and said gaps containing insulating material, and said enclosing means including two flexible diaphragms having a fluid therebetween;

(e) one of said diaphragms permitting coupling to the skin of the animal's body.

17. The lithotrite of claim 16 further characterized in that:

(a) said fluid is water.

18. The lithotrite of claim 16 or 17 further characterized by and including:

(a) compensator means in communication with said fluid between said two diaphragms, adjustment of said compensator means being effective to control the fluid pressure between said diaphragms.

19. The lithotrite of claim 18 further characterized in that:

(a) said compensatory means comprises a vessel which is effective to collect gas bubble formed in said fluid.

20. The lithotrite of claim 18 further characterized by and including:

(a) means for varying the height of the compensator means to control the fluid pressure.

21. The lithotrite of claim 16 further characterized in that:

(a) said spherical cap has an apex angle of at least sixty degrees.

* * * * *